US00PP11572P

United States Patent [19]

Evers

[11] Patent Number: Plant 11,572

[45] Date of Patent: Oct. 17, 2000

[54] SHRUB ROSE PLANT NAMED 'TANOTAX'

[75] Inventor: Hans-Jürgen Evers, Uetersen, Germany

[73] Assignee: Bear Creek Gardens, Inc., Medford, Oreg.

[21] Appl. No.: 09/237,318

[22] Filed: Jan. 26, 1999

[51] Int. Cl.[7] ..... A01H 5/00

[52] U.S. Cl. ..... Plt./107

[58] Field of Search ..... Plt./107, 108, 150, Plt./149, 148

*Primary Examiner*—Howard J. Locker

*Attorney, Agent, or Firm*—Klarquist Sparkman Campbell Leigh & Whinston, LLP

[57] ABSTRACT

Shrub rose plant having resistance against common rose fungal diseases, good winter hardiness, attractive pink flowers, repeat blooming, ease of propagation, and having a plant habit that is somewhat low and spreading.

1 Drawing Sheet

The present invention relates to a new and distinct variety of rose plant of the shrub class which was originated by me by crossing an unnamed seedling with the variety 'Tanilasor'.

The primary objective of this breeding was to produce a new rose variety having resistance against common rose fungal diseases, good winter hardiness, attractive flowers, repeat bloom, and having a plant habit that is somewhat low and spreading. The objective was substantially achieved, along with other desirable improvements, as evidenced by the following unique combination of characteristics that are outstanding in the new variety and that distinguish it from its parents, as well as from all other varieties of which I am aware:

1. Resistant to rose powdery mildew, rust, and blackspot;
2. Production of attractive pink flowers;
3. Repeat blooming;
4. Good winter hardiness;
5. Ease of propogation on its own roots or by budding; and
6. Low and spreading plant habit.

'TANotax' has been tested for cold hardiness in the United States in trials at the Boerner Botanical Garden. It has survived temperatures to −20° F. without supplemental winter protection. 'TANotax' will also produce (in late fall) scattered fruit. They are oval in shape, about ⅝" long and ½" wide. Fully ripe, they are Red Group 44A in color and contain from four to fifteen seeds.

Asexual reproduction of this new variety by cuttings and by budding, as performed at Uetersen, Germany and Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—'Tanilasor'.

Classification:

*Botanical.*—*Rosa hybrida.*

*Commercial.*—Shrub.

FLOWER

Observations made from specimens growth in a garden environment at Uetersen, Germany and at Somis, Calif., January 1996–December 1998.

Blooming habit: Continuous

Bud:

*Size.*—Three-quarter inch long when the petals start to unfurl.

*Form.*—The bud form is pointed ovoid.

*Color.*—When sepals first divide, bud color is Red Group 52A. When half blown, the upper sides of the petals are Red Group 52B; and the lower sides of the petals are Red Group 52B.

*Sepals.*—Color: Green Group 138B. Surface texture: Covered in fine hairs. There are three normally appendaged sepals. There are two unappendaged sepals with hairy edges.

*Receptacle.*—Color: Green Group 137D. Shape: Funnel. Size: Small, about ¼"×¼". Surface: Smooth.

*Peduncle.*—Length: Short, 1 to 1¼ inches. Surface: Glandular. Color: Green Group 137D except when exposed to bright sunlight. It then is Greyed-Purple 183D. Strength: Stiff.

Bloom:

*Size.*—Small. Average open size is 2½ inches.

*Borne.*—Several together in rounded clusters of five to nine blooms.

*Stems.*—Strength: Strong. Average length is about fourteen to sixteen inches.

*Form.*—When first open: High-centered. Permanence: Flattens, all petals curl slightly.

*Petalage.*—Number of petals under normal conditions: 20–25.

*Color.*—The upper sides of the petals are Red Group 52B. The reverse sides of the petals are Red Group 52B. The base of each petal has on both surfaces a small (¼"×¼"), half moon close to Yellow-White. Group 158B in color. The major color on the upper side is Red Group 52B.

*Variegations.*—Occasional white streak on some petals.

*Discoloration.*—The general tonality at the end of the first day: No change. At the end of the third day: A general fading to Red Group 52C. By day five, the color has faded to Red Group 52D.

*Fragrance.*—None.

Petals:

*Texture.*—Thick.

*Shape.*—Round to oval.

*Form.*—Tips slightly recurved.

*Arrangement.*—Imbricated. Petaloids in the center are few (0–4) and small, about ½"×¼". They are Red Group 52B in color and often have a White Group 155A streak on them.

*Persistence.*—Petals drop off cleanly before drying.

*Lastingness.*—On the plant: Short (about five days). As a cut flower: Not tested.

Reproductive parts:

*Anthers.*—Size: Medium. Quantity: Many. Color: Yellow with a pink blush. Arrangement: Regular around styles.

*Filaments.*—Color: Yellow-Orange Group 17D.

*Pollen.*—Color: Orange Group 26B.

*Styles.*—Color: Green-White Group 157B.

*Stigmas.*—Color: Yellow-White Group 158D.

Plant:

*Form.*—Shrub.

*Growth.*—Vigorous, upright, branching, and spreading. At maturity, height is 2½' to 3', width is 2½' to 3'.

Foliage: Number of leaflets on normal mid-stem leaves: five or seven.

*Size.*—Medium (4½ inches long×3½ inches wide).

*Quantity.*—Abundant.

*Color.*—New foliage: Upper and lower surfaces: Greyed-Purple Group 183A. Old foliage: Upper surface: Green Group 139A. Lower surface: Green Group 138A.

Leaflets:

*Shape.*—Pointed oval.

*Texture.*—Leathery.

*Edge.*—Serrated.

*Serration.*—Single, small.

*Petiole rachis.*—Color: Green Group 138A.

*Petiole underside.*—Smooth.

*Stipules.*—Medium (about ½ inch) and bearded.

*Disease resistance.*—Resistant to mildew, blackspot and rust under normal growing conditions.

Wood:

*New wood.*—Color: Greyed-Orange Group 176A. Bark: Smooth.

*Old wood.*—Color: Green Group 137D. Bark: Smooth.

Prickles:

*Quantity.*—On main canes from base: Ordinary. On laterals from main canes: Ordinary.

*Form.*—Medium, hooked downward.

*Color when young.*—Greyed-Purple Group 183A.

*Color when mature.*—Greyed-Orange Group 172B.

Small prickles:

*Quantity.*—On main stalks: None. On laterals: None.

I claim:

1. A new and distinct variety of rose plant of the shrub class, substantially as herein shown and described, characterized particularly by resistance against common rose fungal diseases, good winter hardiness, attractive pink flowers, repeat blooming, ease of propagation, and having a plant habit that is somewhat low and spreading.

* * * * *

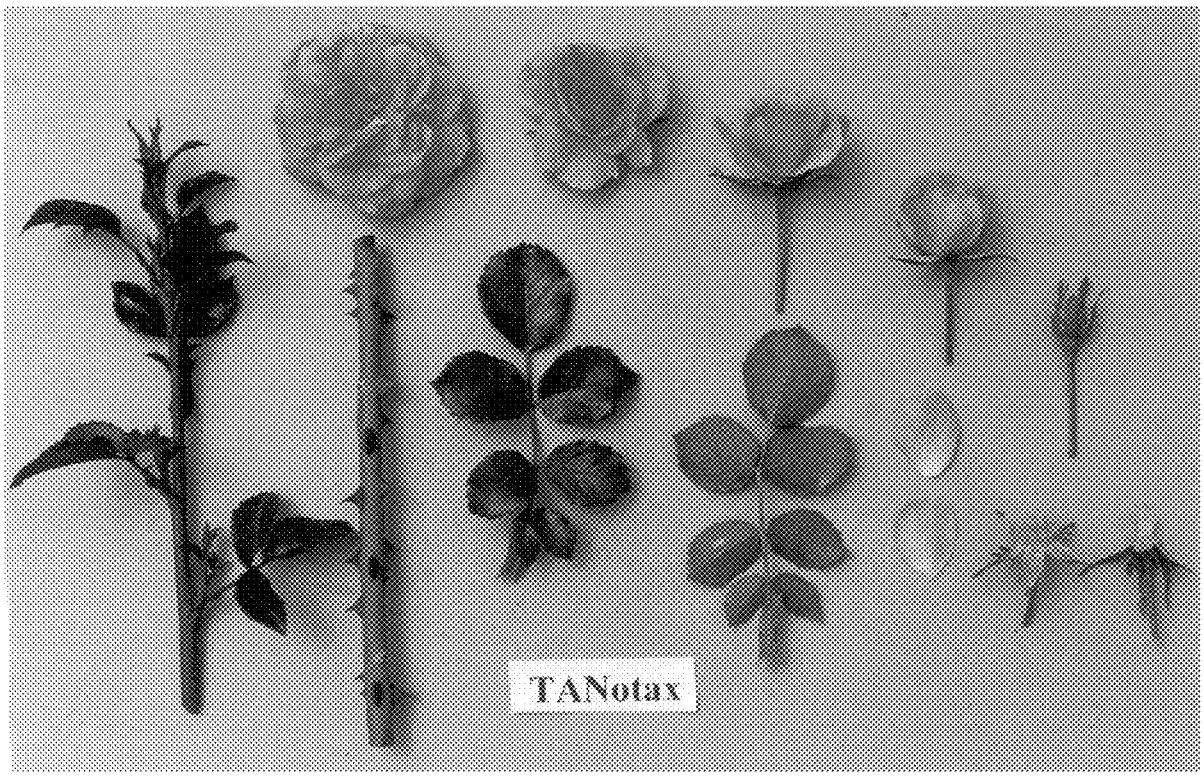
TANotax